United States Patent [19]

Hegde et al.

[11] Patent Number: 5,115,664
[45] Date of Patent: May 26, 1992

[54] TUNABLE FEEDBACK TRANSDUCER FOR TRANSIENT FRICTION MEASUREMENT

[75] Inventors: Suryanarayan G. Hegde, Hollowville; Anthony P. Praino, Poughquag, both of N.Y.; Steven J. Root, Spring Valley, Minn.; Muthuthamby Sri-Jayantha, Ossining, N.Y.

[73] Assignee: IBM Corporation, Armonk, N.Y.

[21] Appl. No.: 543,239

[22] Filed: Jun. 25, 1990

[51] Int. Cl.$^5$ .............................................. G01N 19/02
[52] U.S. Cl. .................................... 73/9; 360/137
[58] Field of Search .................. 360/75, 137; 73/9; 369/53, 58

[56] References Cited

U.S. PATENT DOCUMENTS

| | | |
|---|---|---|
| 4,638,250 | 1/1987 | Shen-Orr et al. |
| 4,646,557 | 3/1987 | Park .................................. 73/9 |
| 4,682,104 | 7/1987 | Lombard et al. |
| 4,695,796 | 9/1987 | Omet et al. |
| 4,697,460 | 10/1987 | Sugiyama et al. |
| 4,720,676 | 1/1988 | Anderson et al. |
| 4,731,579 | 3/1988 | Petersen et al. |

OTHER PUBLICATIONS

Hatamura et al., A Measurement of Sliding Resistance Forces for Various Heads & Disks by High-Rigid Force Sensor, IEEE Trans. on Magnetics, vol. 24, No. 6, Nov. 1988 (pp. 2638-2640).

Hamaguchi et al., Measurement of Impulse Forces Arising from Flying Head/Disk Collision in Magnetic Disk Storage Systems, Proceedings of the International Conference on Advanced Mechatronics, May 21-24, 1989, pp. 257-261.

*Primary Examiner*—Aristotelis Psitos
*Assistant Examiner*—David L. Robertson
*Attorney, Agent, or Firm*—Whitham & Marhoefer

[57] ABSTRACT

A system for measuring transient friction of a head-disk interface in a magnetic disk storage device employs a servo system for accurate measurements. A first movable member carries a slider simulating a magnetic head which rests on a disk when said disk is at rest. The movable member is movably mounted to a second fixed member. A frictionless detector detects a displacement of the movable member relative to a position of the fixed member produced by a force due to friction when the disk spins. A servo system maintains a fixed distance between first and second members in response to an output from the detector and moves the movable member in response thereto. The output is taken from the servo system and provides a signal proportional a force due to friction exerted on said movable member.

10 Claims, 5 Drawing Sheets

TUNABLE FEEDBACK TRANSDUCER FOR TRANSIENT FRICTION MEASUREMENT

BACKGROUND OF THE INVENTION

1. Field of the Invention

The present invention generally relates to the measurement of transient friction at the head-disk interface during spin up of a disk file and, more particularly, to a tunable electro-mechanical or piezoelectric transducer in a servo feedback loop which allows accurate measurement of transient friction.

2. Description of the Prior Art

Accurate characterization of transient friction at the head-disk interface during spin up of a disk file is essential for proper design of lubricated overcoats on recording media, the spindle motor and other associated components of a magnetic disk drive for a computer storage device. Normally, the transient friction is measured using strain gauges which deform proportionally to the transient friction at the head-disk interface. Because of the deformation of the strain gauge, the first measurement is reduced, thus limiting the accuracy with which the friction may be measured. Hatamura et al. in "A Measurement of Sliding Resistance Forces for Various Heads and Disks by High-Rigid Force Sensor", *IEEE Trans. on Magnetics*, Vol. 24, No. 6, Nov. 1988, pp.2638–2640, describe their observations that the force cannot be measured accurately because the present force sensors are so soft that large deformation in measuring disturbs the head assembly. Furthermore, discrepancies between friction data obtained using different strain gauge arrangements has also been found.

SUMMARY OF THE INVENTION

It is therefore an object of the present invention to provide a transducer that allows accurate measurement of head-disk interface friction on a slider during spin up, run time and spin down of a disk drive.

It is another object of the invention to provide a transducer that accomplishes precise and repeatable measurements of head-disk interface friction.

It is a further object of the invention to provide a transient friction transducer which can be constructed at a cost that is an order of magnitude less than current strain gauge-based transducers.

According to the invention, a servo feedback system is provided in which a movable member is connected to a slider that simulates a magnetic head to measure the head-disk interface friction during start up, run time and stopping. The position of the moveable member is monitored by a frictionless detector which detects changes in the position of the moveable member and feeds those changes back through a servo loop to produce an opposite force to balance the force due to friction and thereby limit the movement of the slider. Thus, the servo driving signal is proportional to the force due to friction introduced on the moveable member. In this way, the movable member is held substantially stationary during the measurement of the friction force, eliminating many of the inaccuracies normally associated with strain gauge measurement.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
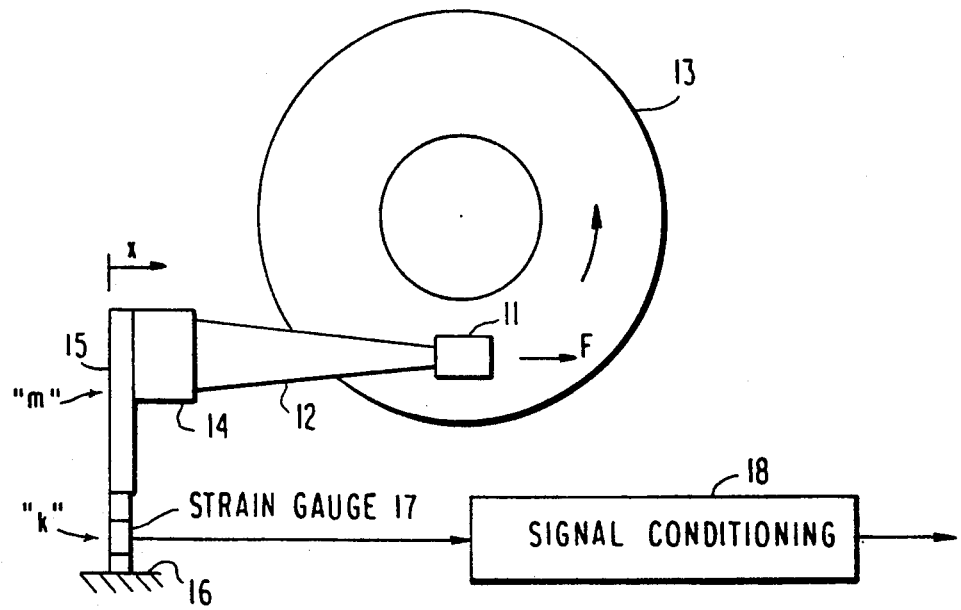
FIG. 1 is a schematic diagram of a typical prior art strain gauge measuring system.

Referring now to the drawings, and more particularly to FIG. 1, there is shown a schematic view of a typical prior art strain gauge transient friction measuring system. A slider 11, simulating a magnetic head, is supported by an arm 12 of the same type and design as the head suspension. The slider 11 is suspended over the surface of a magnetic disk 13 which is adapted to be rotated on a spindle (not shown) in the direction of the arrow. When the disk 13 is not rotating, the slider 11 is at rest and touches the surface of the disk. When the disk 13 is rotated at high speed, the slider 11 "flys" above the surface of the disk cushioned by an air bearing between the disk and the slider. The suspension arm 12 flexes to allow this displacement of the slider (or magnetic head) above the surface of the disk. However, when the disk 13 begins to spin, there can be significant transient friction forces between the slider (or magnetic head) and the disk, and it is desirable to measure those friction forces to determine the effectiveness of lubricants which are used to minimize damage to the head-disk interface.

In the strain gauge measurement system shown in FIG. 1, the suspension arm 12 is attached to a mounting 14 on a beam 15. The beam 15 is, in turn, attached to a fixed support 16 by means of a strain gauge 17. The strain gauge 17 generates an electrical signal proportional to the bending force exerted on it by the beam 15, and this electrical signal is applied to signal conditioning circuits 18 which produces an output signal that provides a measurement of the transient friction between the slider 12 and the disk 13.

Figure 2:
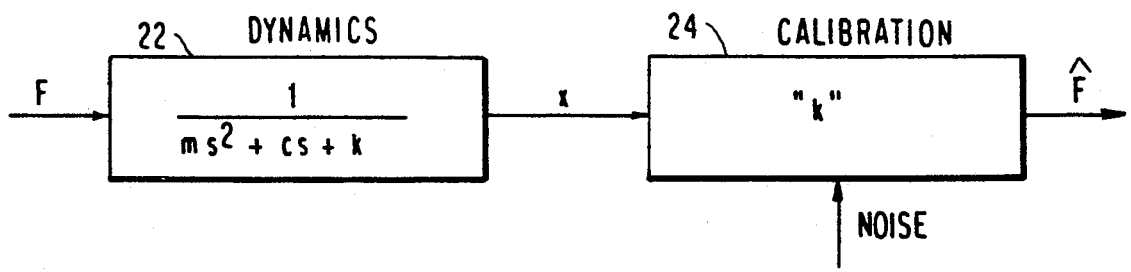
FIG. 2 is a block diagram of the system of FIG. 1 showing the transfer functions of that system.
Figure 3:
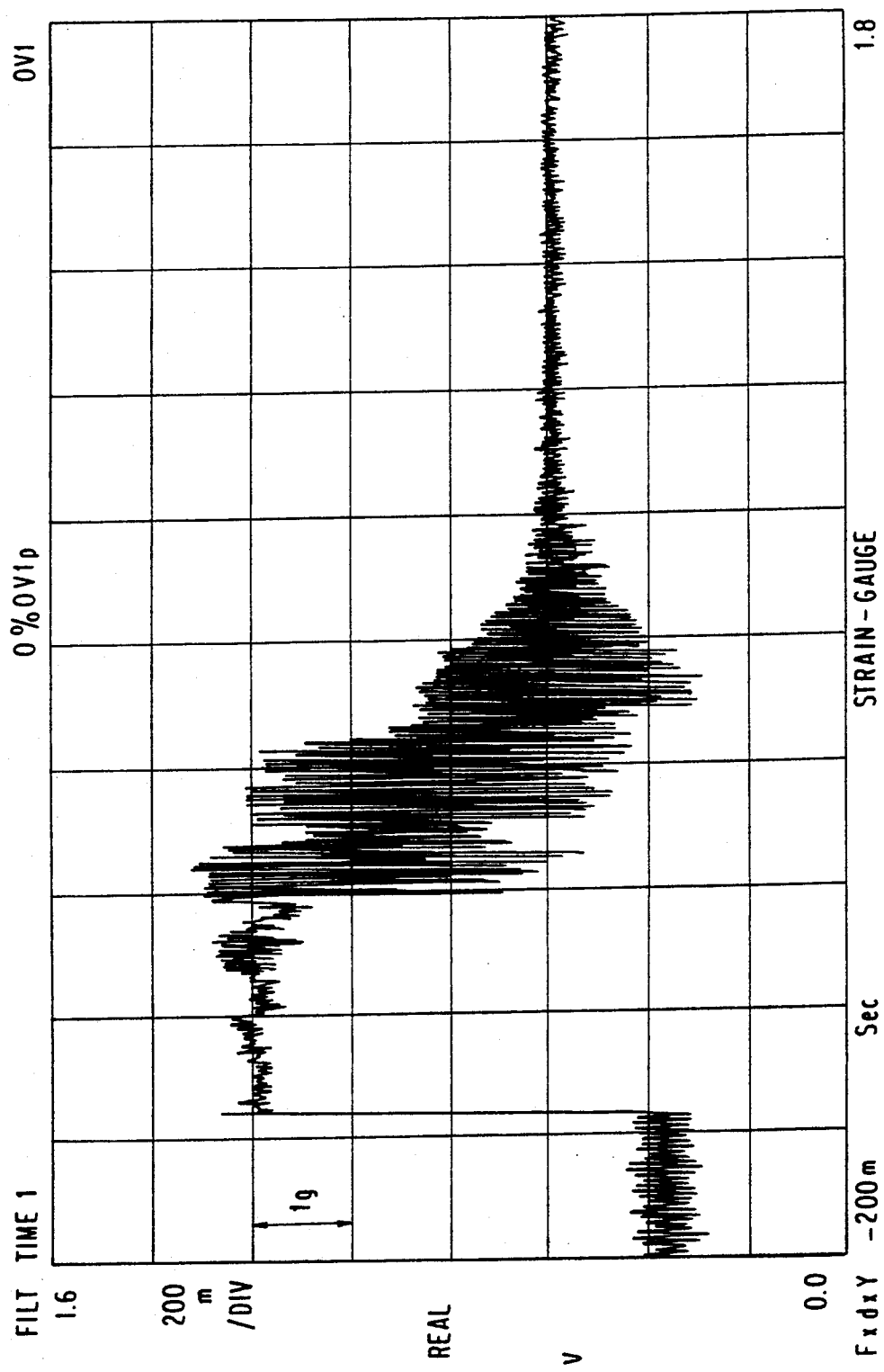
FIG. 3 is a graph showing a typical output friction measurement using the strain gauge system shown system shown in FIG. 1.

The friction, F, as function of time, t, and the displacement, x, represented in FIG. 1 is given by the following equation:

$$F(x, t) = m \frac{d^2x}{dt^2} + c \frac{dx}{dt} + kx, \quad (1)$$

where m is the mass, c is the damping constant and k is the stiffness of the system. The damping constant, c, and the stiffness, k, of the system are typically quite small for bearing type systems. FIG. 2 shows a block diagram of the strain gauge measuring system showing the transfer functions of the principle components. Block 22 represents the dynamics of the system and has a Laplace transform transfer function represented by the following equation:

$$G_P = \frac{1}{ms^2 + cs + k}, \quad (2)$$

where m, c and k are the same constants as defined above. The input to block 22 is the friction, F, and the output is the displacement, x. The displacement, x, is the input to the second block 24 which is the calibration block, the transfer function of which is the constant k. Noise is a second input to block 24, and the output is a measurement of friction, denoted in FIG. 2 as $\hat{F}$. FIG. 3 is a graph showing a typical output signal from the strain gauge measuring system of FIG. 1. It is apparent from this graph that there is considerable sensor dynamics corrupting the signal, making accurate measurement of transient friction impossible. Only an estimate of transient friction can be made from this output, although steady state friction measurements are reasonably accurate Another problem associated with strain gauge measuring systems relates to the repeatability or precision of these systems It is often desirable to perform the friction measurements a plurality of times, cycling through spin up, run time and spin down. The starting frictional force may vary from cycle to cycle depending on how the system stopped at the end of a preceding cycle; that is, the slider 11 may be initially subject to a compressive load or a tensile load or no load at all. This is an unknown variable of the strain gauge measuring systems which prevents fine quantitative transient friction measurements allowing, at best, only qualitative measurements.

Figure 4:
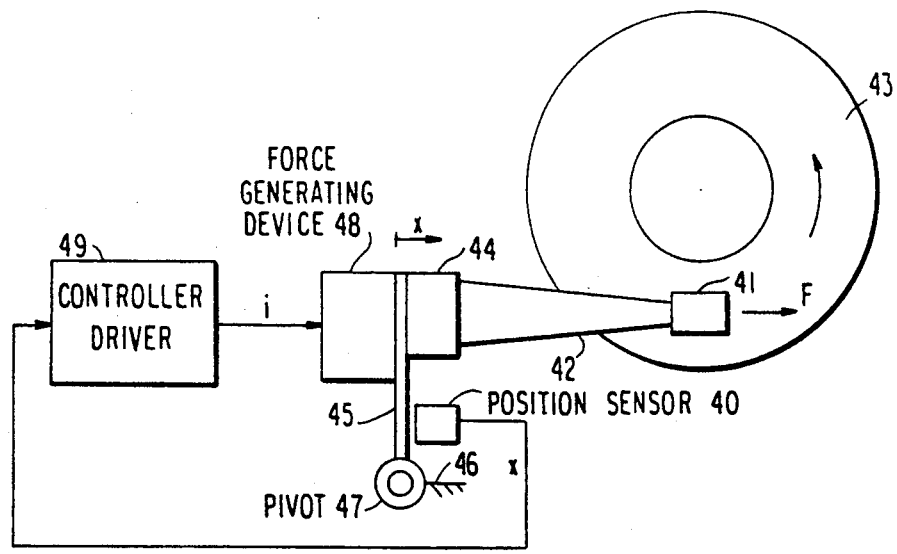
FIG. 4 is a schematic diagram of the feedback transducer measuring system according to the invention.

Turning now to FIG. 4, there is illustrated a block diagram of the new feedback transducer system according to the present invention. This system also includes slider 41, simulating a magnetic head, is supported by an arm 42 of the same type and design as the head suspension. The slider 41 is suspended over the surface of a magnetic disk 43 which is adapted to be rotated on a spindle (not shown) in the direction of the arrow. The suspension arm 42 is attached to a mounting 44 on a beam 45. The beam 45 is, in turn, attached to a fixed support 46; however, the attachment of the beam 45 to the fixed support 46 is by means of a bearing or pivot 47. Attached to the same end of the beam 45 as the mounting 44 is a force generating device 48 the purpose of which is to apply a force to the beam 45 which is equal to but in a direction opposite the direction of the frictional force F, thereby minimizing the displacement x. The force generating device 48 is driven by a controller driver 49 which receives an input signal proportional to the displacement x from a position sensor 40. Thus, the sensor 40, the force generating device 48 and the controller driver 49 form a position servo loop which balances the force due to friction The driving signal to the force generator is therefore proportional to the friction, F, to be measured.

Figure 5:
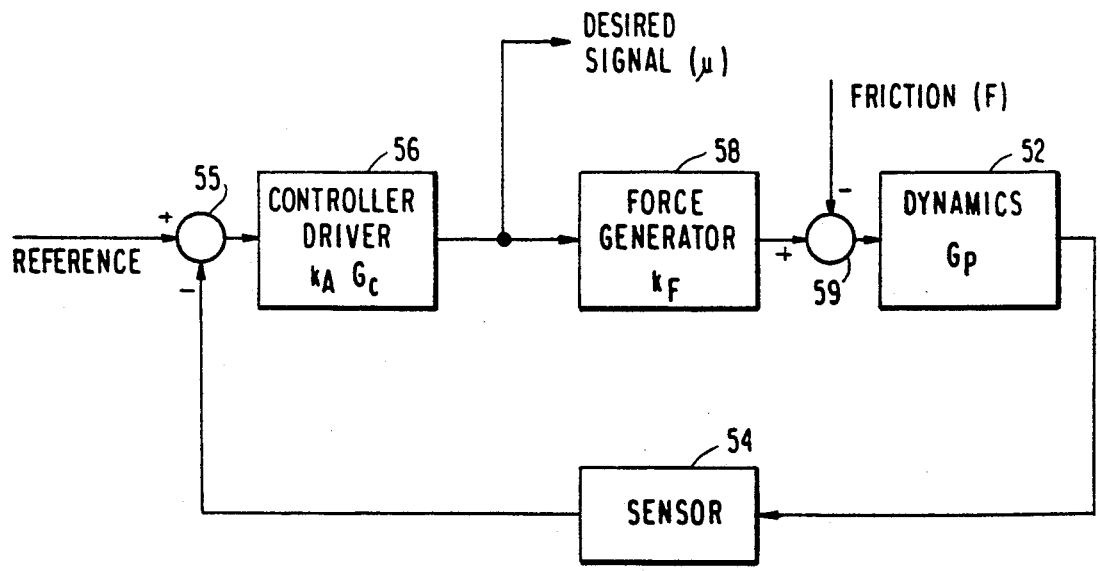
FIG. 5 is a block diagram of the system of FIG. 4 showing the transfer functions of the new system.

The friction, F, as function of time, t, and the displacement, x, represented in FIG. 1 is given by the following equation:

$$F(x, t) = m\frac{d^2x}{dt^2} + c\frac{dx}{dt} + kx + k_Fi, \quad (3)$$

where i is the driving signal to the force generating device 48 and k, is a force constant having the dimensions newtons/amp or newtons/volt, depending on whether the signal i is a current or a voltage, respectively. FIG. 5 shows a block diagram of the feedback transducer measuring system according to the invention showing the transfer functions of the principle components. Block 52 represents the dynamics of the system and has a Laplace transform which is the same as equation (2). As before, the output of this block is the displacement, x, which is sensed by the sensor 54 and fedback as a negative input to the summing junction 55, the other input of which is a reference signal.

The sensor 54 is a frictionless sensor so as not to effect the friction measurement being made. This may be an optical system, such as a light emitting diode (LED), reflector and phototransistor combination or a laser interferometer, an eddy current sensor, a capacitive sensor, or an ultrasonic sensor, for example. The choice of the sensor depends on the specific implementation of the invention. The reference signal is typically zero to establish a position of the slider which is maintained by the servo loop. However, the reference signal may be a varying signal to cause the slider to move with respect to the disk for the purpose of some measurements.

The output of the summing junction 55 is an error signal which is supplied to the controller driver 56 having a transfer function of $k_A G_c$. $k_A$ is an amplifier gain and is tunable. This tunable gain controls the compliance of the device. The controller 56 is a proportional-integral-derivative (PID) type controller, known in the servo arts, and its transfer function is given by the following equation:

$$G_c = K_P + K_D s + K_I/s, \quad (4)$$

where $k_P$ is the proportional gain, $k_D$ is the derivative gain, and $k_I$ is the integral gain.

The output of the controller driver 56 is applied to the force generator 58 having a transfer function of $k_F$. The output of the force generator 58 is applied to the summing junction 59 to balance the force due to friction, F. The desired output signal, u, is taken at the output of the controller driver 56.

Figure 6:
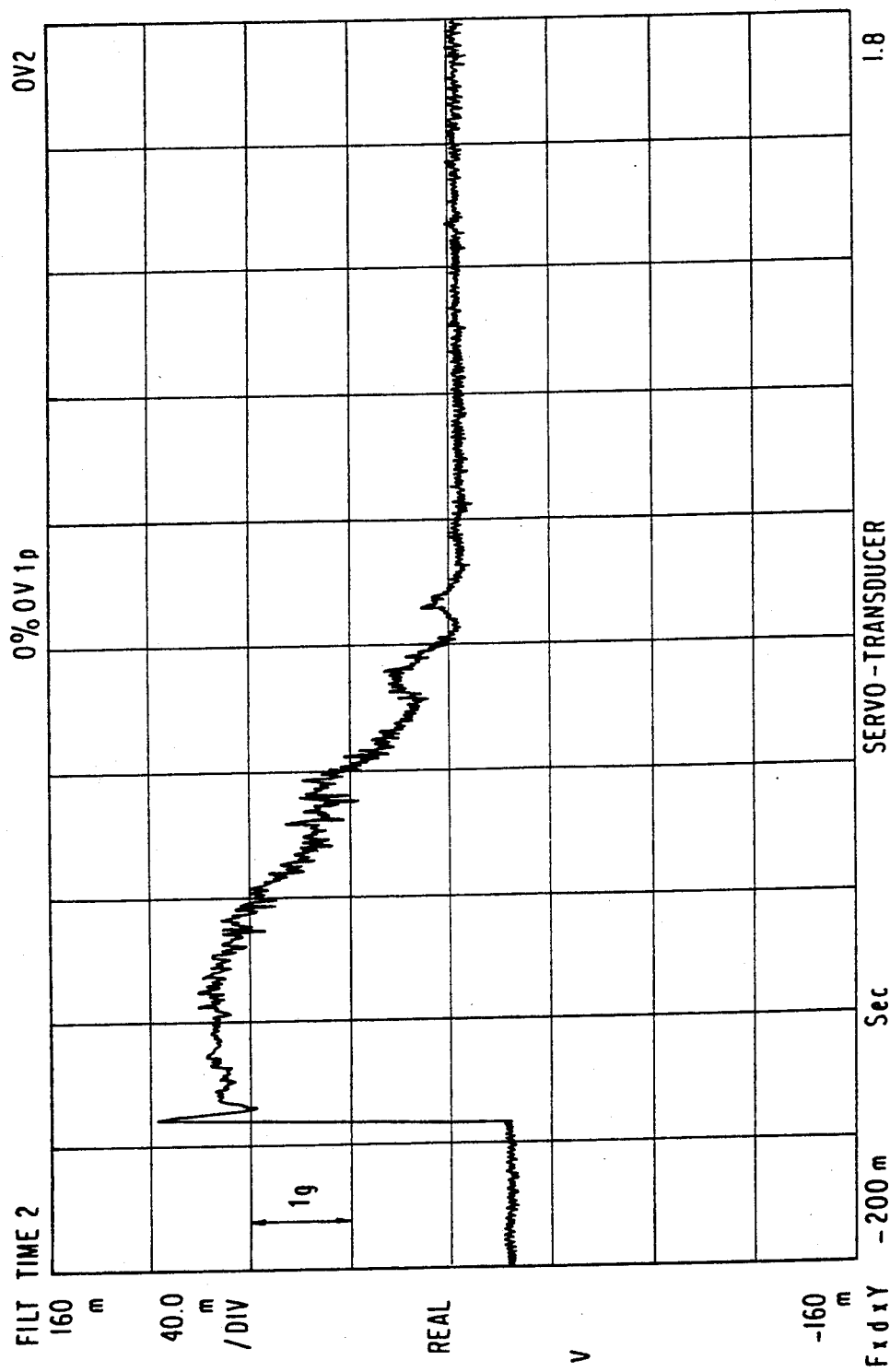
FIG. 6 is a graph showing a typical output friction measurement using the feedback transducer measuring system according to the invention.

FIG. 6 is a graph showing a typical output signal from the feedback transducer measuring system of FIG. 4. It is apparent from this graph that the resulting signal is considerably cleaner and unaffected by sensor dynamics than that obtained from the strain gauge measuring system. The result is a marked increase in the precision and accuracy in the measurement of the transient friction of the head-disk interface.

Figure 7:
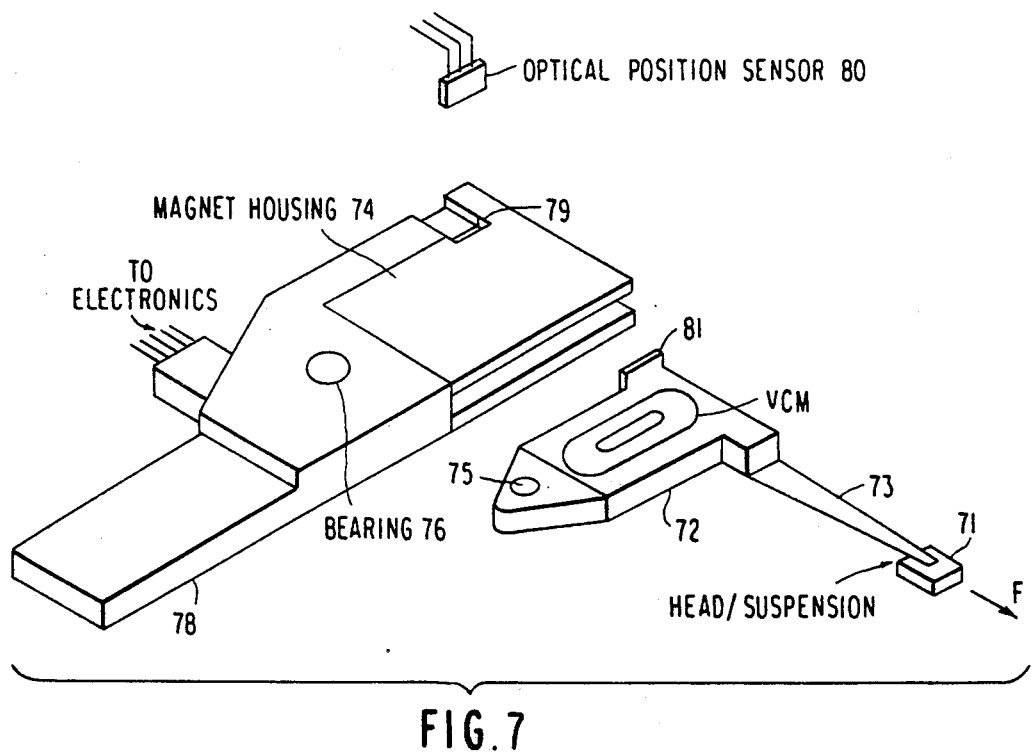
FIG. 7 is an exploded view of a preferred embodiment of the new transducer using an electro-mechanical force generator.

FIG. 7 is an exploded view of a preferred embodiment of a transducer according to the invention using an electro-mechanical force generator. In FIG. 7, the slider 71 is attached to a voice coil motor (VCM) armature mount 72 via a suspension arm 73. It is important in this implementation of the invention that the VCM armature mount 72 be made of nonmagnetic material. A suitable material is aluminum with a voice coil armature of copper wire. The VCM armature mount 72 is adapted to be inserted between a pair of VCM magnets (not shown) within a magnet housing 74 and attached at pivot point 75 to a bearing 76 in the mount 78 carrying the magnet housing 74. The mount 78 has a slot or relief 79 adapted to receive an optical position sensor 80, which may typically be an LED (light emitting diode) and a phototransistor to receive reflected light from the LED. The VCM armature mount 72 is provided with a reflector 81 which reflects the light from the LED to the phototransistor, thereby providing a measure of the displacement, x.

The bearing 76 is preferably a ball bearing providing a single pivot point for the VCM mount 72; however, other bearing structures may be used. Linear ball bearing structure having three contact points may be used. Instead of ball bearings, flexure suspensions may be used allowing for linear or substantially linear movement of the VCM mount. Alternatively, a gas bearing may be used. Whatever bearing structure that is used should have minimum friction so as not to degrade from the accuracy of measurement of the transient friction force between the head-disk interface.

Figure 8:
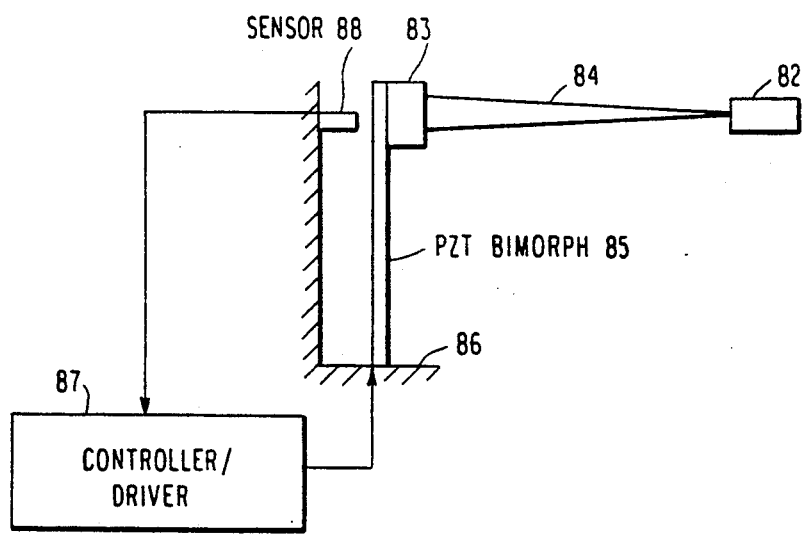
FIG. 8 is a schematic representation of an alternative embodiment of the invention using a piezoelectric force generator.

While the voice coil motor provides a convenient and inexpensive force generator, other force generators may also be used. An alternative implementation of the feedback transducer according to the invention is illustrated in FIG. 8. In the implementation, the slider 82 is attached to a mount 83 via a suspension arm 84. The mount 83 is attached to a bimorphous piezoelectric beam 85 attached to a fixed support 86, and it is caused to bend or flex in a direction opposite to the force due to friction on the slider 83 by a voltage output signal from the controller driver 87. A sensor 88 is attached to the fixed support for detecting the displacement, x, caused by the force due to friction on the slider 83. The sensor 88 may be, for example, a capacitive type sensor. The signal generated by the sensor 88 is supplied as the input signal to the controller driver 87. Thus, it will be appreciated that the servo system shown in FIG. 8 is the equivalent of that shown in FIG. 7.

While the invention has been described in terms of a preferred embodiment and an alternative implementation, those skilled in the art will recognize that the invention can be practiced with modification within the spirit and scope of the appended claims.

Having thus described our invention, what we claim as new and desire to secure by Letters Patent is as follows:

1. A system for measuring transient friction of a head-disk interface in a magnetic disk storage device comprising:
   a first movable member carrying a slider simulating a magnetic head which rests on a disk when said disk is at rest;
   a second fixed member to which said movable member is movably attached;
   frictionless detector means for detecting a displacement of said movable member relative to a position of said fixed member produced by a force due to friction when disk begins to spin;
   servo means for maintaining a fixed distance between said first and second members in response to an output from said detector; and
   output means connected to said servo means for generating a signal proportional a force due to friction exerted on said movable member.

2. A system according to claim 1 wherein said first movable member carries an armature and is mounted to pivot around a fixed point in a housing and said second fixed member comprises said housing and includes magnets which interact with said armature.

3. A system according to claim 2 wherein said frictionless detector means comprises an optical position sensor.

4. A system according to claim 3 wherein said optical position sensor is a light emitting diode reflecting off a reflector on said movable member to a phototransistor.

5. A system according to claim 3 wherein said servo means comprises:
   a controller which converts an output of said optical position sensor into an electronic signal; and
   a driver which converts said electronic signal into a driving current which is applied to said armature to produce a force that opposes said force due to friction, said output means being connected to receive said electronic signal.

6. A system according to claim 1 wherein said first movable mount comprises a piezoelectric member which moves in a direction opposite to said force due to friction in response to a driving signal from said servo means.

7. A system according to claim 6 wherein said servo means comprises:
   a controller which converts an output of said frictionless detector means into an electronic signal; and
   a driver which converts said electronic signal into a driving voltage applied to said piezoelectric member to produce a motion that opposes a motion caused by said force due to friction, said output means being connected to receive said electronic signal.

8. A system according to claim 1 wherein said frictionless detector means comprises an optical position sensor.

9. A system according to claim 8 wherein said optical position sensor is a light emitting diode reflecting off a reflector on said movable member to a phototransistor.

10. A system according to claim 1 wherein said frictionless detector means comprises a capacitive position sensor.

* * * * *